United States Patent [19]

Coco et al.

[11] Patent Number: 4,469,951
[45] Date of Patent: Sep. 4, 1984

[54] METHOD AND APPARATUS FOR TANNING OR UV TREATMENT

[76] Inventors: Eugene E. Coco; Willie L. Scott, both of 804 Central Ave., Hot Springs, Ark. 71901

[21] Appl. No.: 431,628

[22] Filed: Sep. 30, 1982

[51] Int. Cl.³ .............................................. A61N 5/06
[52] U.S. Cl. ............................ 250/494.1; 250/504 R; 250/454.1; 128/371
[58] Field of Search ............. 250/494.1, 503.1, 504 R, 250/453.1, 454.1, 455.1; 128/371

[56] References Cited

FOREIGN PATENT DOCUMENTS 2112787 10/1972 Fed. Rep. of Germany ...... 128/371
2319409 11/1974 Fed. Rep. of Germany ...... 128/371

*Primary Examiner*—Alfred E. Smith
*Assistant Examiner*—Jack I. Berman
*Attorney, Agent, or Firm*—Neal J. Mosely

[57] ABSTRACT

A method of tanning or treatment with ultraviolet radiation consists of providing a source of artificial ultraviolet radiation; providing a motor powered turntable in juxtaposition to the source of artificial ultraviolet radiation; energizing the source of artificial ultraviolet radiation; positioning an individual or object to be irradiated on the turntable; and energizing the motor of the turntable to rotate it for a selected period of time. The sources of artificial ultraviolet radiation are preferably elongated fluorescent sun lamps which provide separate sources of UVA and UVB radiation. The turntable is rotated at least one complete revolution during the selected time that the individual or object is positioned thereon and more preferably at a rate of one revolution per minute. The sun lamps may be energized for the same selected period of time as the turntable, although when both UVA and UVB lamps are provided, the timers allow a lesser amount of time for the UVB radiation than for the UVA radiation. Preferably, the turntable and the UVA lamp are energized by the same timer controlled circuit and the UVB lamp is energized by a separate timer controlled circuit.

20 Claims, 3 Drawing Figures

U.S. Patent  Sep. 4, 1984  4,469,951
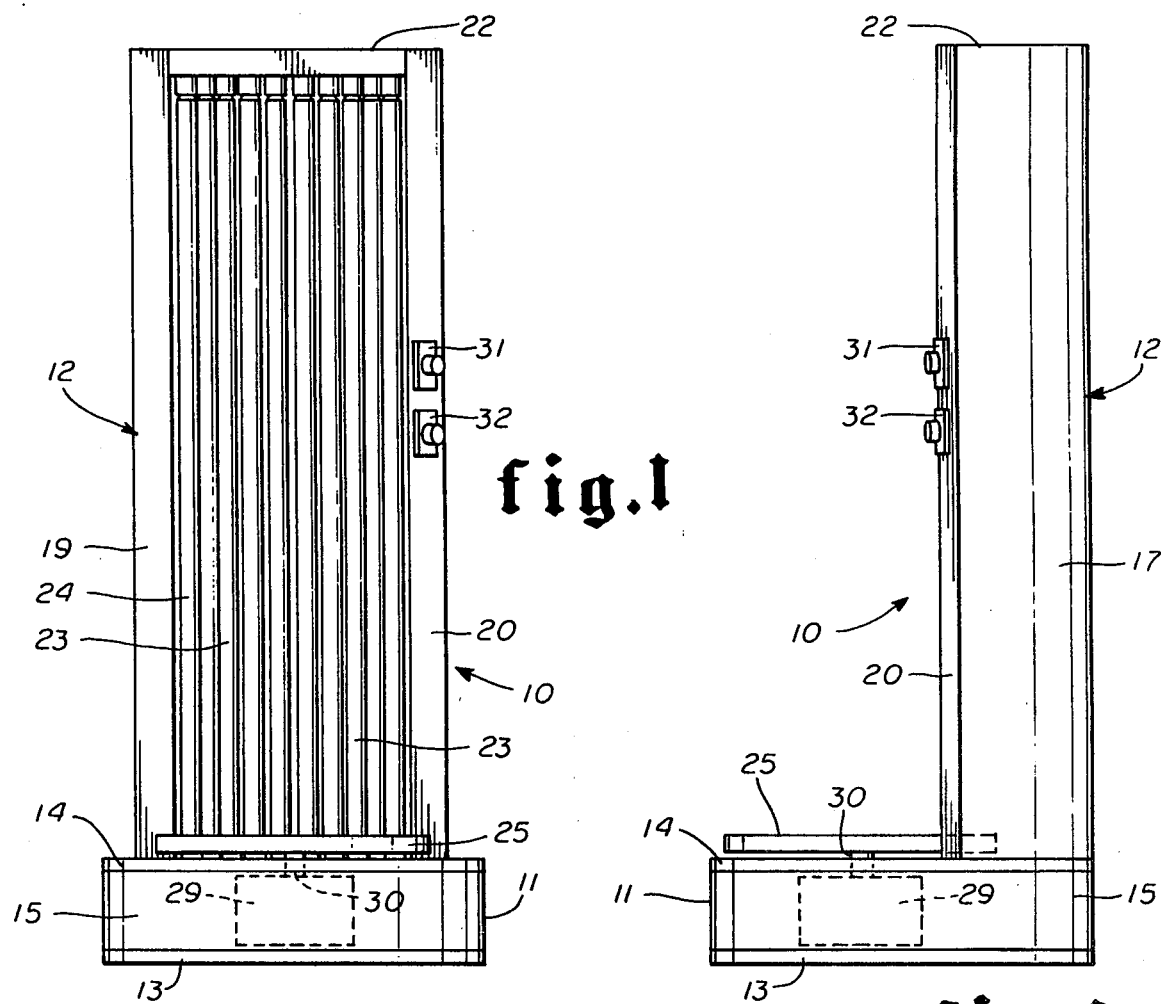
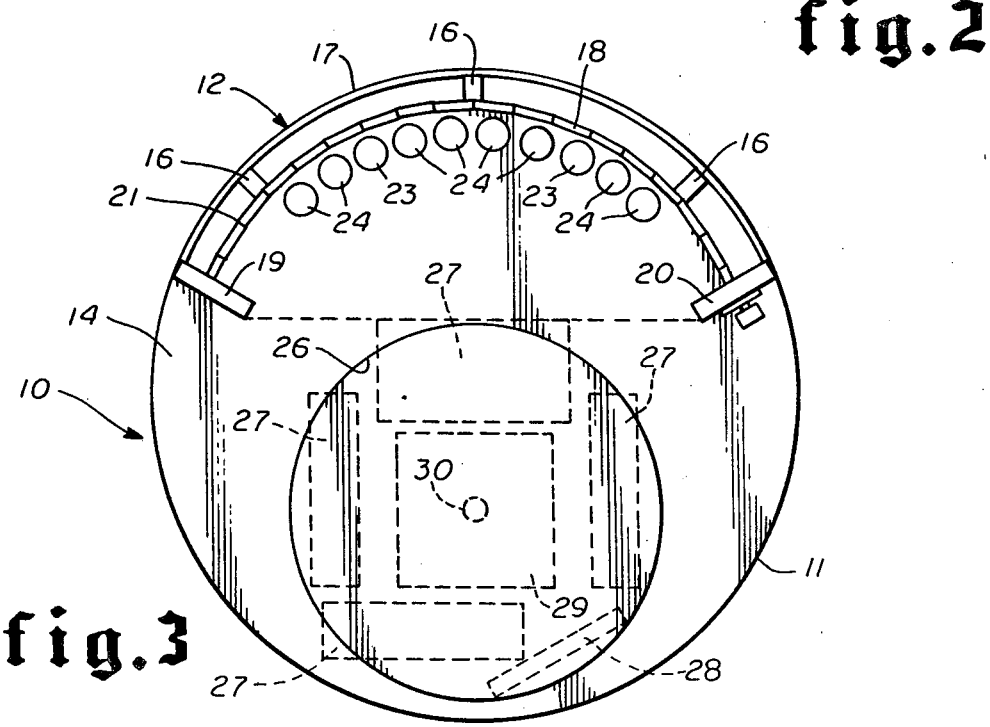

METHOD AND APPARATUS FOR TANNING OR UV TREATMENT

BACKGROUND OF THE INVENTION

1. Field of the Invention

This invention relates to new and useful improvements in methods and apparatus for tanning or irradiation of individuals or objects by artificial sources of ultraviolet radiation.

2. Brief Description of the Prior Art

Tanning of individuals and UV irradiation of objects by natural sunlight is well known. The use of natural sunlight, however, is subject to the objection that it is irregular and varies considerably with the weather, the season of the year, and the geographical location.

Incandescent UV lamps have been known and used for indoor tanning and for UV irradiation. More recently, fluorescent UV lamps have been available and particularly UV lamps which give radiation concentrated in the UVA and UVB regions, respectively.

Indoor tanning by means of suitable UV lamps has been accomplished by several different means, each of which has had some drawbacks. The simplest system of indoor tanning or irradiation involves exposure to a single general purpose UV lamp. This does not permit selective exposure to the UVA and UVB radiation and may be quite irregular in application.

Another system uses a number of UV lamps of any desired type and a system of mirrors which concentrate the radiation in a select region of the individual or object being treated.

Still another system uses spaced parallel banks of UV lamps with a bed or support for an individual to be positioned between the banks of lamps. Both of these systems suffer from irregularity of irradiation and lack of control.

SUMMARY OF THE INVENTION

One of the objects of this invention is to provide a new and improved method of tanning or irradiation of persons or objects by artificial ultraviolet radiation.

Another object of the invention is to provide a method in which a person or object is rotated before a source of artificial ultraviolet radiation for a selected time.

Still another object of the invention is to provide a method in which a person or object is rotated on a time controlled turntable before a bank of ultraviolet lamps.

Still another object of the invention is to provide a method in which a person or object is rotated on a turntable before a bank of UVA and UVB lamps in which the operation of the turntable and UVA lamps are timed together and the UVB lamps are timed separately.

Another object of the invention is to provide an apparatus for performing a new and improved method of tanning or irradiation of persons or objects by aritificial ultraviolet radiation.

Another object of the invention is to provide an apparatus in which a person or object is rotated before a source of artificial ultraviolet radiation for a selected time.

Still another object of the invention is to provide an apparatus in which a person or object is rotated on a time controlled turntable before a bank of ultraviolet lamps.

Still another object of the invention is to provide an apparatus in which a person or object is rotated on a turntable before a bank of UVA and UVB lamps in which the operation of the turntable and UVA lamps are timed together and the UVB lamps are timed separately.

Other objects of the invention will become apparent from time to time throughout the specification and claims as hereinafter related.

The foregoing and other objects of the invention are accomplished by a method of tanning or treatment with ultraviolet radiation (and the apparatus for performing the method) which consists of providing a source of artificial ultraviolet radiation; providing a motor powered turntable in juxtaposition to the source of artificial ultraviolet radiation; energizing the source of artificial ultraviolet radiation; positioning an individual or object to be irradiated on the turntable; and energizing the motor of the turntable to rotate it for a selected period of time.

The sources of artificial ultraviolet radiation are preferably elongated fluorescent sun lamps which provide separate sources of UVA and UVB radiation. The turntable is rotated at least one complete revolution during the selected time that the individual or object is positioned thereon and more preferably at a rate of one revolution per minute. The sun lamps may be energized for the same selected period of time as the turntable, although when both UVA and UVB lamps are provided, the timers allow a lesser amount of time for the UVB radiation than for the UVA radiation. Preferably, the turntable and the UVA lamp are energized by the same timer controlled circuit and the UVB lamp is energized by a separate timer controlled circuit.

BRIEF DESCRIPTION OF THE DRAWINGS

FIG. 1 is a view in front elevation of an apparatus for tanning or ultraviolet irradiation in accordance with this invention.

FIG. 2 is a view in side elevation of the apparatus of FIG. 1.

FIG. 3 is a plan view of the apparatus of FIG. 1 showing some details of the connections for the UV lamps and the turntable.

DESCRIPTION OF THE PREFERRED EMBODIMENT

Referring to the drawings by numerals of reference there is shown an improved apparatus for uniform tanning or treatment with ultraviolet radiation. The apparatus 10 consists of a supporting base 11 of generally cylindrical construction having an arcuate supporting wall 12 extending upward therefrom. The shape of the base and the upwardly extending supporting wall are matters of choice and design, although the design shown is considered to be an attractive commercial design for the equipment.

Supporting base 11 has circular or disc shaped bottom wall 13 and top wall 14 joined and supported by cylindrical side wall 15. While the particular dimensions are a matter of choice, based on the dimensions of some of the components, base 11 is preferably 33" in diameter and about 6½" deep.

Supporting wall 12 extends for about 150° of arc of the periphery of base 11 and is about 75" high. Supporting wall 12 includes three vertical studs 16 (preferably 1"×1½") which support the back covering 17 at the rear and mirror 18 at the front. The ends of wall 12 have vertical moldings 19 and 20, preferably about ¾"×4½" in cross section.

Mirror 18 is generally arcuate in shape but is creased along a plurality of crease lines 21 which cause the shape to be polygonal. The mirror 18 is preferably of a highly polished, mirror finish, aluminum material. Wall 12 is closed at the top by cover piece 22 which supports the upper connections for the UV lamps, as will be subsequently described.

A source of artificial ultraviolet radiation is provided in the apparatus in the form of a plurality of elongated UV lamps supported by wall 12 in front of mirror 18. Lamps 23 are elongated, preferably 72" long, UVB fluorescent lamps. Lamps 24 are elongated, preferably 72" long, UVA fluorescent lamps. Any suitable UVA and UVB lamps may be used, although Westinghouse F72T12BL-S/HO UVA lamps and Westinghouse FS72T2 UVB lamps are suitable for this equipment. These UV lamps are controlled by conventional circuits and time switches as described below.

A motor powered turntable 25 is supported in base 11 in juxtaposition to the source of artificial ultraviolet radiation, viz. lamps 23 and 24, and is adapted to support an individual or object for rotation thereon for irradiation by the lamps. Base 11 has a circular opening 26 in top wall 14, below which there is positioned the motor for rotating turntable 25. In this particular apparatus, opening 26 is 19½" in diameter and turntable 25 is 20" in diameter.

Within the base 11, there are located the ballasts 27 for the UV lamps 23 and 24 and the terminal board 28. Motor 29 is positioned below opening 26 and supports turntable 25 on shaft 30. Motor 29 is a ruggedly constructed motor and supporting structure of the type used for heavy revolving advertising displays. A preferred motor assembly is the MOTIONDISER manufactured by Young Electro-Mechanical Company, Inc. of Bensenville, Ill. The MODEL500 RB supports weights up to 300 lb., on discs up to 36" diameter and is capable of rotation at speeds up to 3 RPM. In the operation of this equipment, the turntable 25 must rotate at least once during the time that the UV lamps are energized and preferably at a rate of one revolution per minute.

End molding 20 of wall 12 has a pair of timer switches 31 and 32 supported thereon for controlling the operation of the apparatus. These timer switches are of conventional design and are available commercially at most electrical supply stores. Timer switch 31 is connected in circuit (a conventional circuit, not shown) with motor 29 and UVA lamps 24. Motor 29 and lamps 24 will therefore be energized together for the same selected period of time. Timer switch 32 is connected in circuit (a conventional circuit, not shown) with UVB lamps 23.

OPERATION

The description which has been given above is of the equipment which is to be used in carrying out the improved method of this invention. This is a method of tanning or treatment with ultraviolet radiation which comprises providing a source of artificial ultraviolet radiation, viz. lamps 23 and 24; providing a motor powered turntable 25 in juxtaposition to the source of artificial ultraviolet radiation (lamps 23 and 24); energizing the source of artificial ultraviolet radiation; positioning an individual or object to be irradiated on turntable 25; and energizing the motor 29 of turntable 25 to rotate the same for a selected period of time. Rotation must be at least once during the time of UV radiation exposure, although a rotation of one RPM is desirable.

In carrying out this method the preferred source of artificial ultraviolet radiation are elongated fluorescent sun lamps 23 and 24, providing UVB and UVA radiation, respectively. UVA radiation produces light to moderate tanning, without much danger of burning (sunburning), but does not provide protection against future burning. UVB radiation can burn if more than about 15 minutes exposure is used. UVB radiation, however, in light exposures, gives relatively permanent tanning and ultimately complete protection against burning.

In the preferred embodiment of this method, both the UVA and UVB lamps are used. The individual, without clothing, stands on turntable 25 and turns on switch 31 which energizes motor 29 to operate turntable 25 at one RPM (or other suitable setting) and simultaneously energizes UVA lamps 24. Timer switch 31 can be set from times up to 30 minutes, although shorter times are generally preferred for safety. Timer switch 32 can then be set for a shorter time, not in excess of 20 minutes, to energize the UVB lamps 23.

The method therefore consists of rotating the individual on turntable 25 for the selected time exposed to either the UVA or the UVA and UVB lamps. Rotation in front of only the UVB lamps can be accomplished by substituting UVB lamps for the UVA lamps controlled by turntable switch 31. This, however, should be done only with extreme caution because of the danger of burning on early excessive exposure to UVB radiation. The method of rotating an individual on turntable 25 in front of UV lamps to produce uniform exposure, and the controlled use of UVA and UVB lamps is quite safe when carried out according to instructions. The result is the production of a uniform tan without burning.

While this invention has been described fully and completely, with special emphasis on a single preferred embodiment, it should be understood that, within the scope of the appended claims, this invention may be practiced otherwise that as specifically set forth herein.

I claim:
1. A method of tanning or treatment with ultraviolet radiation which comprises
    providing a source of artificial ultraviolet radiation extending vertically for a distance of about the height of the person or object being irradiated and extending arcuately in closely spaced relation,
    providing a motor powered turntable in juxtaposition to said source of artificial ultraviolet radiation and having its center positioned substantially equidistant from said radiation source and unobstructed on the side away from said radiation source for safe exit therefrom while in operation,
    energizing said source of artificial ultraviolet radiation for a selected period of time,
    positioning an individual or object to be irradiated on said turntable, and
    energizing the motor of said turntable to rotate the same for a selected period of time.
2. A method according to claim 1 in which
    said source of artificial ultraviolet radiation comprises a plurality of closely spaced elongated fluorescent sun lamps.
3. A method according to claim 1 in which said turntable is rotated at least one complete revolution during the selected time that the individual or object is positioned thereon.

4. A method according to claim 1 in which
said turntable is rotated at least one revolution per minute during the selected time that the individual or object is positioned thereon.

5. A method according to claim 1 in which:
said source of artificial ultraviolet radiation is energized for the same selected period of time as said turntable.

6. A method according to claim 1 in which
said source of artificial ultraviolet radiation comprises a source of predominantly UVA radiation.

7. A method according to claim 1 in which
said source of artificial ultraviolet radiation comprises a source producing a substantial amount of UVB radiation.

8. A method according to claim 1 in which
said source of artificial ultraviolet radiation comprises separate sources of substantial amounts of UVA and UVB radiation.

9. A method according to claim 8 in which
said source of UVB radiation is separately energized for a lesser time than said source of UVA radiation.

10. A method according to claim 8 in which
said source of UVB radiation is energized for a lesser timer than said source of UVA radiation and said source of UVA radiation is energized for the same selected time as said turntable.

11. An apparatus for tanning or treatment with ultraviolet radiation which comprises
a source of artificial ultraviolet radiation extending vertically for a distance of about the height of the person or object being irradiated and extending arcuately in closely spaced relation,
a motor powered turntable in juxtaposition to said source of artificial ultraviolet radiation adapted to support an individual or object to be irradiated for rotation thereon and having its center positioned substantially equidistant from said radiation source and unobstructed on the side away from said radiation source for safe exit therefrom while in operation,
circuit means for energizing said source of artificial ultraviolet radiation for a selected period of time, and
circuit means for energizing the motor of said turntable to rotate the same for a selected period of time.

12. An apparatus according to claim 11 in which
said source of artificial ultraviolet radiation comprises a plurality of closely spaced elongated fluorescent sun lamps.

13. An apparatus according to claim 11 including
timing means operable to rotate said turntable at least one complete revolution during the selected time that an individual or object is positioned thereon.

14. An apparatus according to claim 11 in which
the motor of said turntable rotates said turntable at least one revolution per minute during the selected time that an individual or object is positioned thereon.

15. An apparatus according to claim 11 including
timing means operable to energize said source of artificial ultraviolet radiation for the same selected period of time as said turntable.

16. An apparatus according to claim 11 in which
said source of artificial ultraviolet radiation comprises a source of predominantly UVA radiation.

17. An apparatus according to claim 11 in which
said source of artificial ultraviolet radiation comprises a source producing a substantial amount of UVB radiation.

18. An apparatus according to claim 11 in which
said source of artificial ultraviolet radiation comprises separate sources of substantial amounts of UVA and UVB radiation.

19. An apparatus according to claim 18 including
separate timing means for said sources of UVA and UVB radiation operable to energize said UVB radiation for a lesser time than said source of UVA radiation.

20. An apparatus according to claim 19 in which
said source of UVA radiation timing means comprises said turntable timing means, and
said source of UVB radiation timing means comprises a separate timer having a maximum time period substantially shorter than the maximum time period of said turntable timing means.

* * * * *